United States Patent [19]

Young et al.

[11] Patent Number: 5,240,585
[45] Date of Patent: Aug. 31, 1993

[54] CONDUCTIVE BRIDGE FOR EXTERNAL CONTROL OF ELECTROOSMOTIC FLOW

[75] Inventors: James E. Young, La Honda, Calif.; Jurgen A. Lux, Niederkirchen, Fed. Rep. of Germany

[73] Assignee: Hewlett-Packard Company, Palo Alto, Calif.

[21] Appl. No.: 914,174

[22] Filed: Jul. 14, 1992

[51] Int. Cl.$^5$ .................... G01N 27/26; G01N 27/447
[52] U.S. Cl. .............. 204/299 R; 204/180.1; 204/182.1
[58] Field of Search ............ 204/299 R, 180.1, 182.1; 138/146; 65/60.4, 60.6

[56] References Cited

U.S. PATENT DOCUMENTS

| 4,705,616 | 11/1987 | Andresen et al. | 204/299 R |
| 4,842,701 | 6/1989 | Smith et al. | 204/180.1 |
| 4,936,974 | 6/1990 | Rose et al. | 204/299 R |
| 4,940,883 | 7/1990 | Karger et al. | 219/200 |
| 5,092,972 | 3/1992 | Ghowsi | 204/180.1 X |
| 5,151,164 | 9/1992 | Blanchard et al. | 204/180.1 X |
| 5,180,475 | 1/1993 | Young et al. | 204/180.1 |

FOREIGN PATENT DOCUMENTS 55-40048 10/1981 Japan.
1312907 7/1991 Japan.

*Primary Examiner*—John Niebling
*Assistant Examiner*—John S. Starsiak, Jr.

[57] ABSTRACT

An electrophoresis system for controlling electroosmotic flow by affecting a zeta potential, wherein a conductive bridge provides continuity of control. A conductive coating on an optically transparent capillary tube is made of an opaque material which is removed at a detection window for on-column detection of sample constituents past the window. The conductive coating may be allowed to float relative to ground, may be grounded, or may be connected to one or more high voltage power supplies so that a potential gradient is established along the length of the conductive coating. A bridge establishes a low resistance electrical connection across the detection window, thereby establishing a continuity of external control of electroosmotic flow. In a first embodiment, the bridge is a generally flat metallic member that is adhesively bonded to the capillary tube at opposite ends of the detection window. The metallic member includes an aperture along the optical path from the on-column detector to the window. In a second embodiment the bridge is a wire that is bonded to the conductive coating at opposite ends of the window. A third embodiment is to leave a portion of the conductive coating along the length of the window at a region outside of the optical path. Another embodiment is one in which the detection window is at ground potential and the on-column detector itself is used to provide a bridge.

19 Claims, 5 Drawing Sheets

CONDUCTIVE BRIDGE FOR EXTERNAL CONTROL OF ELECTROOSMOTIC FLOW

TECHNICAL FIELD

The present invention relates generally to electrophoretic systems and more particularly to providing a continuity of control of electroosmotic flow along a capillary column.

BACKGROUND ART

Applications for electrophoresis, an analytical technique for separating and identifying constituents in a sample, include the determination of a sample's purity, the determination of molecular weights for proteins and nucleic acids, the mapping of nucleic acid primary structures, i.e. DNA and RNA sequence analyses, and the definition of phenotypic variance of a protein at the molecular level. Electrophoretic techniques rely on the fact that each molecular species has a unique combination of mass, size, shape, charge, density and sub-unit structure, all of which result in mobility differences responsive to an electric field. Various electrophoretic techniques use one or more of these properties to cause varying degrees of molecular separation via the migration of molecular species under an electric field.

Capillary electrophoresis is a technique using a capillary tube which is filled with a conductive fluid, as for example a buffer solution. A small amount of sample is introduced at one end of the capillary tube, whereafter a high potential difference is applied across the ends of the tube. Electroosmotic flow and differences in electrophoretic mobilities combine to provide a spatial separation of constituents of the sample solution at the outlet end of the capillary tube.

Electroosmotic flow is the movement of a liquid relative to a stationary charge surface as a result of electric fields applied to the liquid. U.S. Pat. No. 4,936,974 to Rose et al. explains electroosmotic flow as a result of charge accumulation at the interior capillary surface due to preferential adsorption of anions from the buffer solution that fills the bore of the capillary tube. The negative charge of the anions attracts a thin layer of mobile positively charged buffer ions which then accumulate adjacent to the inner surface. The charge accumulation at the interior wall provides a radially extending electric field. The potential across this radially extending electric field is referred to as the "zeta potential." The longitudinally extending electric field that is applied across the capillary tube attracts the positive ions which are hydrated by water toward a grounded outlet end of the capillary tube, viscously dragging other hydrated molecules. This dragging of molecules applies to neutral and negatively charged molecules, as well as positively charged molecules. The result is a bulk flow of the sample in the buffer solution toward the grounded outlet end of the capillary tube. Consequently, electroosmotic flow provides a means for moving neutral and negatively charged constituents of a sample toward a ground electrode.

Electrophoretic migration is the movement of charged constituents in response to an electric field applied along the longitudinal axis of the capillary tube. A positively charged molecule will be accelerated through the electroosmotic flow toward the ground electrode. Negatively charged molecules may be repelled by the ground electrode, but the force of the electroosmotic flow overcomes the repulsion and advances the negatively charged molecules.

As a result of the combination of electroosmotic flow and electrophoretic migration for an analysis in which a positive electrode is applied to the inlet end of the capillary tube and a ground electrode is applied to the outlet end, a spatial separation will occur with positively charged constituents exiting first, followed by neutral constituents and then negatively charged constituents. Each constituent of a sample may be identified by detecting the time required for the constituent to travel through the capillary tube. The quantity of the constituent within the sample is determined by the height and/or area of a signal trace on an electropherogram during a period of detection of that constituent.

An "on-column detector" detects migration of sample constituents past a detection area of the capillary tube between the inlet end and the outlet end. Ultraviolet and fluorescence on-column detectors are common. Alternatively, detection can take place after release of the sample from the outlet end, i.e., "off-column detection." For example, U.S. Pat. Nos. 4,705,616 to Andresen et al. and 4,842,701 to Smith et al. describe electrospraying the separated solution from the outlet end for off-column detection by mass spectrometry.

Obtaining an accurate analysis requires that each sample constituent be moved to the detection area. Often, the sample is introduced into the inlet end of the capillary tube by insertion of the inlet end into a sample vial, whereafter the inlet end is inserted into a first buffer vial electrically connected to a high voltage electrode. The outlet end of the capillary tube is inserted into a buffer reservoir vial connected to the ground electrode. Upon initiating the separation procedure, a negatively charged molecule may be drawn into the first buffer vial before electroosmotic flow can take full effect. Thus, these molecules will not be detected, rendering the analysis less accurate. Another problem in obtaining an accurate analysis involves the resolution of constituent detections. If a sample contains a number of constituents having similar electrophoretic mobilities, an analysis may be susceptible to errors in identifying and in quantifying the constituents. Yet another problem involves external factors, such as atmospheric conditions, that may have an effect on the electrophoretic separation.

U.S. patent application Ser. No. 07/754,797, to Young et al. which is assigned to the assignee of the present application and is incorporated herein by reference, describes a system and method for controlling electroosmotic flow and reducing undesired effects of external influences, thereby improving the analytic procedure. The rate of electroosmotic flow is directly proportional to the permittivity of the solution, the longitudinal axial electrical field and the zeta potential and is inversely proportional to the viscosity of the solution. Young et al. teach that the zeta potential can be controlled by providing a coating of electrically conductive material on the outside wall of the capillary tube. The conductive coating reduces the likelihood that an undesired voltage gradient will be created along the outside wall. A controlled field along the outside wall prevents external forces from affecting the internal ionic charge at the interior wall of the capillary tube. The electrically conductive coating may be allowed to float, but preferably is grounded to reduce the likelihood of electrostatic charges on the outside wall of the capillary tube.

An object of the present invention is to provide a capillary column of an electrophoresis system having on-column detection capability, wherein the capillary column provides improved control of electroosmotic flow.

SUMMARY OF THE INVENTION

The above object has been met by a capillary column that includes a conductive external coating on an optically transparent capillary tube and includes a low resistance electrical path across a slit in the external coating. The slit in the external coating defines an optical path for on-column detection of sample constituents past a detection area and the electrical path across the slit provides an electrical continuity for optimizing an influence on electroosmotic flow.

The conductive external coating need not extend to the ends of the optically transparent capillary tube. Often an inlet end of the tube is inserted into one liquid reservoir, while an outlet end is inserted into a second liquid reservoir. A high voltage for creating an electric field along the longitudinal axis of the capillary tube is connected by inserting a first electrode in the first reservoir and a second electrode in the second reservoir. Because the liquid is conductive, a potential difference applied to the first and second electrodes is impressed across the length of the capillary tube. An external coating extending to the inlet and outlet ends would provide an electrical short between the charged liquid reservoirs. Thus, in this embodiment the coating should not extend to the inlet and outlet ends.

The conductive coating is also removed at a predefined detection area of the capillary column, thereby allowing on-column detection. Removal of the external coating at the detection area provides an optical path for an ultraviolet detector, fluorescence detector or the like. The problem caused by this removal of the external coating at the optical path is that the optimal influence on electroosmotic flow is rendered more difficult. As described above with reference to patent application Ser. No. 07/754,797 to Young et al., the conductive external coating may be allowed to float. A slit coating may then include first and second portions of different potentials. This is not a desirable situation. Alternatively, Young et al. teach that the detection area should be as close to the outlet end of a capillary tube as possible, so that rather than having a slit external coating, the outlet end may have an extended area that is left uncoated to accommodate optical coupling to a detector. However, this leaves a significant portion of the capillary tube without a means for influencing electroosmotic flow. Another alternative is described in Japanese Application No. Sho 55-40048 to Okubo as providing a conductive coating which is optically transparent. Unfortunately, transparent conductive coatings on a capillary tube are not readily achievable.

Continuity of flow control is achieved in the present invention by use of a bridge which does not block the optical path for on-column detection, but provides a conductive path across a slit between first and second portions of the external coating. In one embodiment, the bridge is a conductive member, such as a brass or aluminum device, having a generally flat surface and an aperture aligned with the slit in the external coating. Conductive adhesive secures the first portion of the external coating to the device at one side of the aperture, while the second portion is attached to the device at the opposite side of the aperture, again using conductive adhesive.

A second embodiment of the present invention is one in which the bridge is formed by one or more wires that extend across the slit without interference with the optical path for on-column detection. For example, a bond wire conventionally used to couple an input/output pad on an integrated circuit chip to a supporting structure may be used as a bridge wire. It is also possible to fabricate the bridge wire by merely removing a portion of the external coating at the predefined detection area, leaving a portion that does not interfere with the optical path but which provides the required electrical path.

Another embodiment of the present invention is to provide an optically transparent but electrically conductive material within the slit that defines the on-column detection area of the capillary column.

An advantage of the present invention is that the use of the bridge permits a designer to locate a detection window anywhere along the capillary column. In comparison, the above-identified application to Young et al. limits placement of an on-column detector to an extreme end of the capillary column. The bridge provides the continuity that is desirable in order to achieve optimal electroosmotic flow control.

BEST MODE FOR CARRYING OUT THE INVENTION

Figure 1:
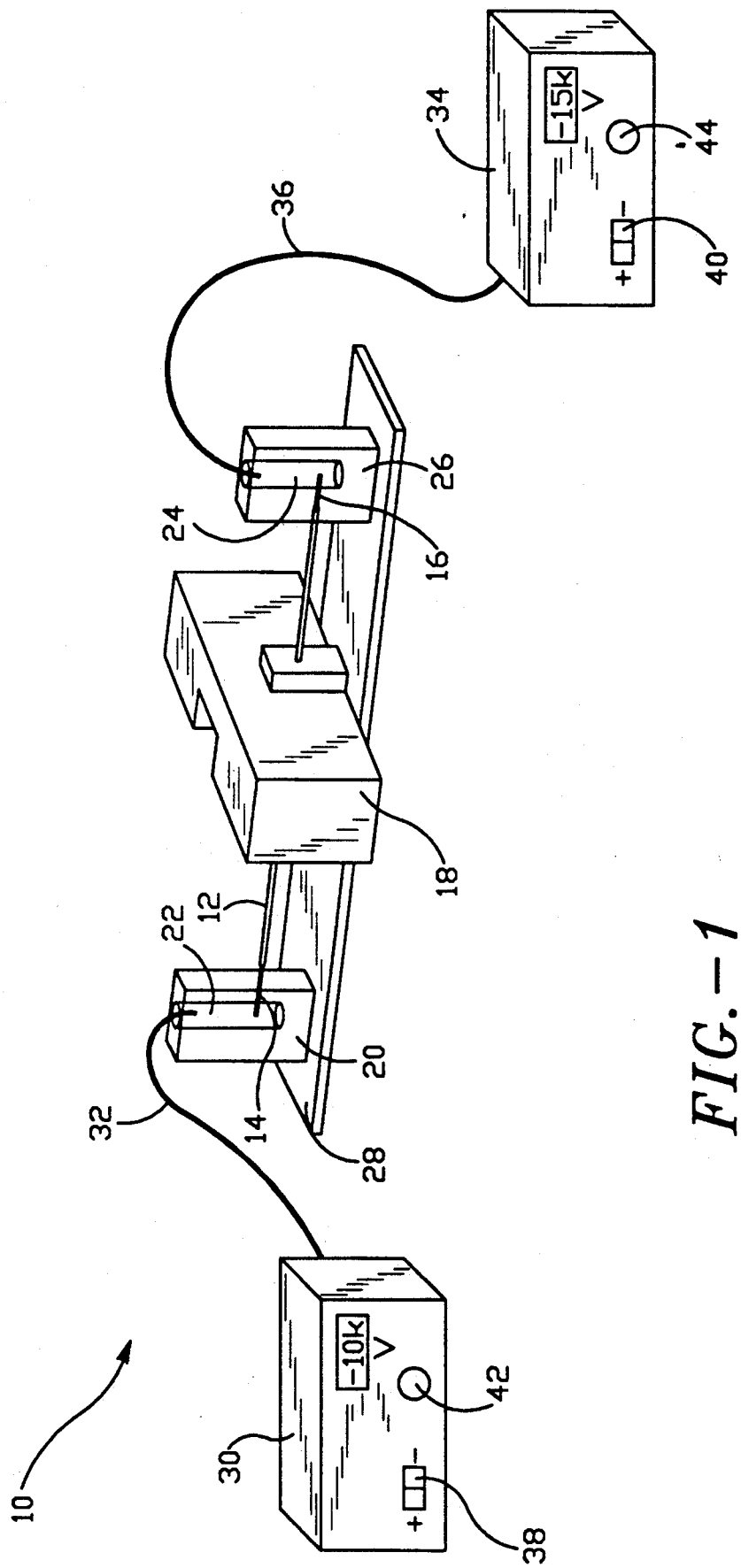
FIG. 1 is a schematic view of an electrophoresis system having on-column detection and having external control structure for affecting the rate of electroosmotic flow through a capillary tube of the system.

With reference to FIG. 1, an electrophoretic system 10 is shown as including a capillary tube 12 having an inlet end 14 and an outlet end 16. The capillary tube is of the type known in the art. A fused silica tube having a coating of polyimide may be used. Such a capillary tube is flexible but has a material memory that urges the tube to return into a generally straight condition after flexing. The capillary tube has an inside diameter of 50 microns and an outside diameter that is typically in the range of 140 microns to 360 microns, but these dimensions are not critical.

An on-column detector 18 is located along the length of the capillary tube 12. The polyimide coating is removed from the capillary tube at the optical coupling of the tube to the detector. U.S. Pat. No. 4,940,883 to Karger et al. describes a device for removing a polymer from a portion of a capillary tube to provide a detection window for on-column detection. In capillary zone electrophoresis, ultraviolet absorbance detectors are commonly used, but other detectors are known. For example, detection may also occur using a chemiluminescence, refractive index, or conductivity detector. The optical coupling of the detector to the capillary tube permits detection of movement within the capillary tube.

The inlet end 14 of the capillary tube 12 is inserted into a container 20 having a supply vial 22. At the opposite side of the detector 18 is a buffer reservoir vial 24 that is in fluid communication with the outlet end 16 of the capillary tube. The buffer reservoir vial is housed within a container 26. The two containers 20 and 26 and the detector 18 are shown as resting on a table 28.

A first high voltage power supply 30 is electrically connected to the supply vial 22 via a power line 32 that represents an anode electrode. The first power supply 30 provides a high voltage, shown in FIG. 1 as −10 k volts, at the supply vial 22. However, this high voltage is not the potential difference across the capillary tube 12. The potential difference is determined by the voltage at the buffer reservoir vial 24. This voltage is provided by a second high voltage power supply 34 in electrical communication with the buffer reservoir vial 24 via a power line 36 that represents the cathode electrode. The second power supply 34 is illustrated as being set to provide a second high voltage of −15 k volts. Thus, the potential difference across the capillary tube 12 is 5 k volts. A standard potential gradient in capillary zone electrophoresis is 200 v/cm. To achieve this standard, the length of the capillary tube 12 would then be 25 cm.

Each of the high voltage power supplies 30 and 34 is a bipolar device having a polarity-select switch 38 and 40 to adjust the polarity of the associated electrode 32 and 36. Voltage-adjustment dials 42 and 44 allow a user to accurately set the outputs of the power supplies. The rate of electroosmotic flow through the capillary tube 12 may be varied while maintaining the same potential gradient by providing corresponding adjustments of the first and second power supplies 30 and 34. That is, a change in the voltage offset relative to ground changes the electroosmotic flow rate and, therefore, the time required to complete an analysis of a particular sample. For example, using the electrophoresis system of FIG. 1 in which the capillary tube has an inside diameter of 50 microns and an outside diameter of 140 microns, with the respective voltages set at −15 k volts and −10 k volts, a particular analysis requires a migration time of eighty minutes. By varying the voltage offset upwardly relative to ground, the flow rate is increased, so that the same analysis can take place in a much shorter time, e.g., seventeen minutes where each power supply is increased by 15 k volts to ground and +5 k volts. A corresponding negative adjustment to the two power supplies, i.e. a decrease in the voltage offset relative to ground, decreases the electroosmotic flow rate.

Figure 2:
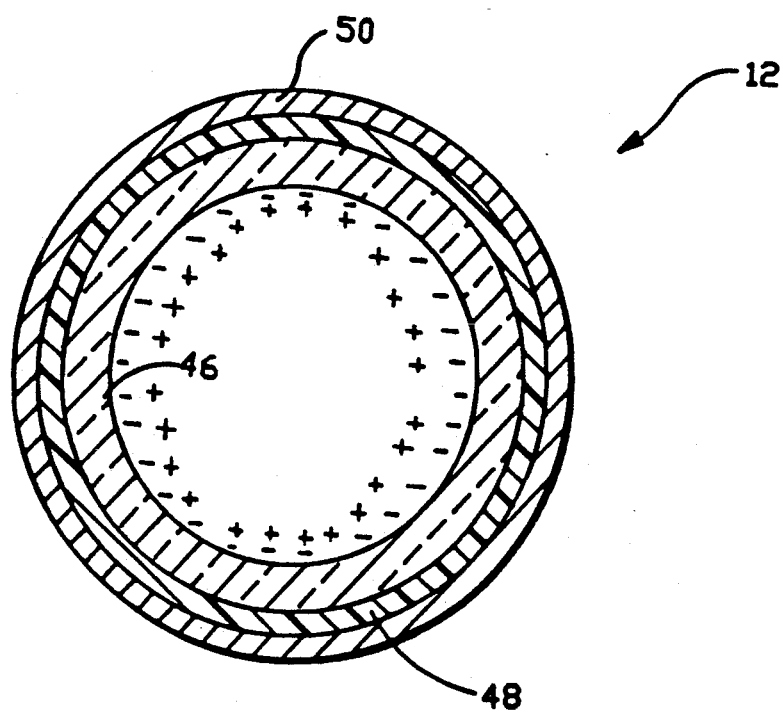
FIG. 2 is a side sectional view of the capillary tube of FIG. 1.

In addition to an adjustment of the voltage offset relative to ground, electroosmotic flow rate can be affected by providing a conductive coating to the capillary tube 12. Referring now to FIG. 2, the capillary tube 12 is shown as including a fused silica capillary layer 46, and a polyimide layer 48. These two layers 46 and 48 are standard in the art. The capillary tube 12 also includes a conductive coating 50. By "conductive coating" what is meant is a coating that may be used to establish or to eliminate an electrical field along the capillary tube, wherein the means of establishing or eliminating the electrical field is by electrical conduction. The conductive coating 50 of the capillary tube 12 may be a nickel print on a standard polyimide layer 46. However, other materials may be utilized. Alternatively, the layers 48 and 50 may be combined into a single layer to provide a conductive polymer. For example, a cross-linked polyimide containing 7.5 percent carbon black may be used.

The two high voltage power supplies described above provide an electrical field along the longitudinal axis of the capillary tube 12. A radially extending electrical field is also created. As illustrated by the symbols "+" and "−", charge accumulation at the interior capillary surface results from preferential adsorption of anions from the buffer solution that fills the migration path of the capillary tube. The negative charge of the anions attracts a thin layer of mobile positively charged buffer ions. The electrical potential is referred to as "zeta potential." Electroosmotic flow is a direct result of this double layer of ions formed on the interior capillary surface. Consequently, any charge at the exterior of the capillary tube has a potential of affecting ion collection and electroosmotic flow.

Referring to FIGS. 1 and 2, the conductive coating 50 on a capillary tube 12 may be allowed to "float" relative to ground. The conductive coating decreases the likelihood of an electrostatic field developing about the exterior of the capillary tube. Such a field would reduce the reliability of an electrophoretic analysis, since it would cause a variation of the zeta potential along the length of the capillary tube.

Rather than allowing a conductive coating 50 of the capillary tube 12 to float, it would be preferred to ground the conductive coating. In addition to creating a reference point to the voltage offset provided by the high voltage power supplies 30 and 34, the grounding of the conductive coating would potentially increase the surface zeta potential. Since zeta potential affects the electroosmotic flow rate, increasing the zeta potential increases the flow rate.

A difficulty with providing electroosmotic flow control by means of a conductive coating on a capillary tube 12 involves the continuity of the control across an on-column detection area. Typically, the conductive coating is an opaque material that must be removed at a detection window to provide an optical path through the capillary tube.

Figure 3:
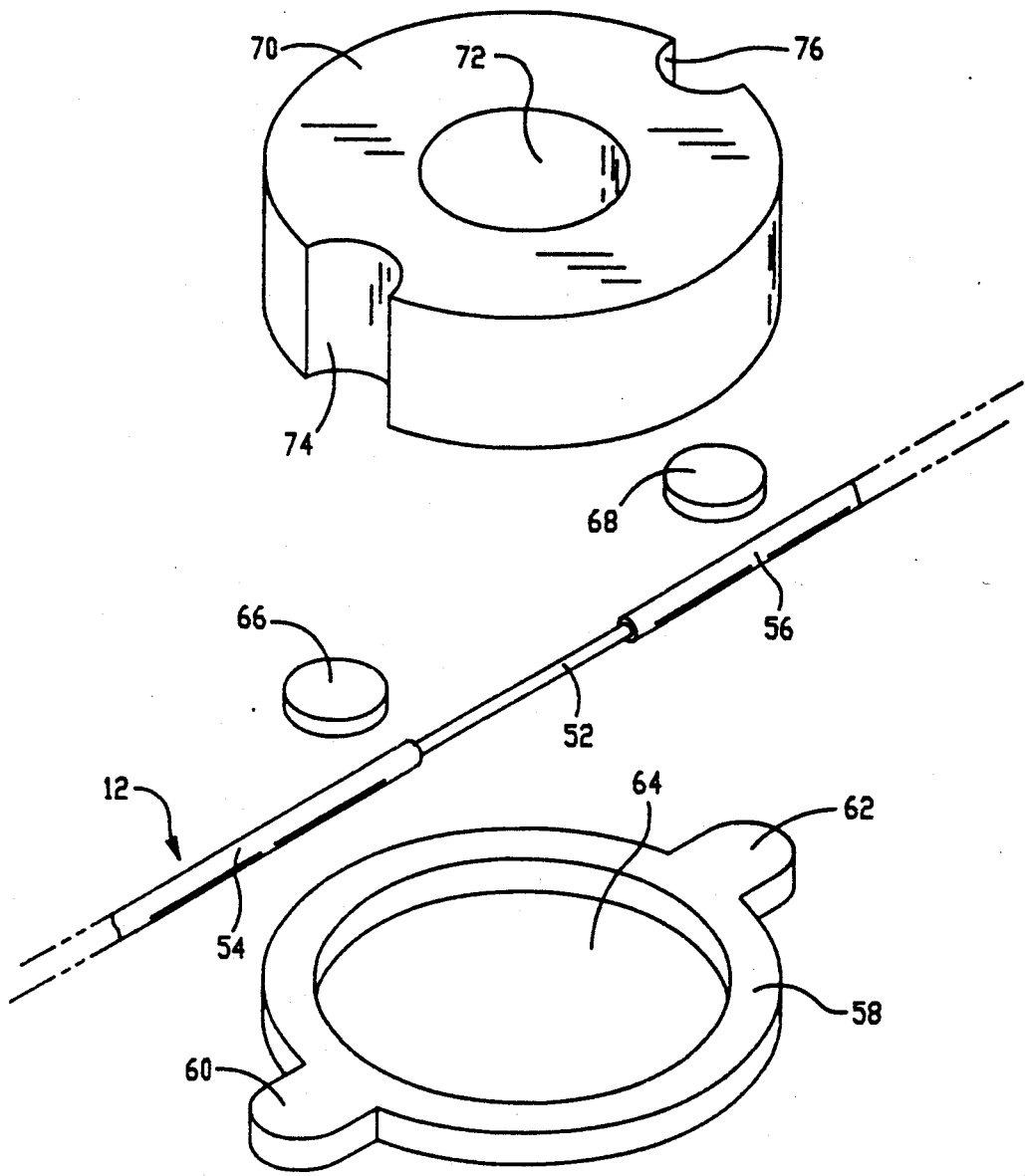
FIG. 3 is an exploded view of a first embodiment of a conductive bridge for ensuring continuity of the external control structure of FIG. 1.
Figure 4:
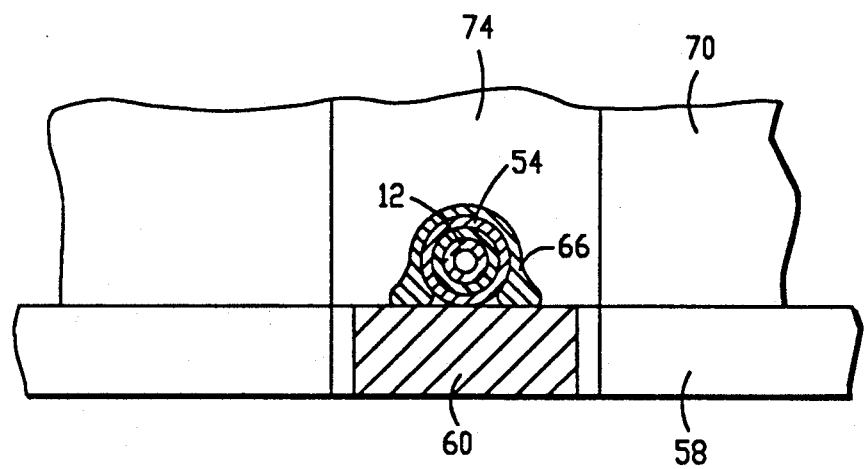
FIG. 4 is a side sectional view of the embodiment of FIG. 3.

Referring now to FIGS. 3 and 4, the removal of the conductive coating from a capillary tube 12 to form a detection window 52 defines first and second portions 54 and 56 of the conductive coating. Incidentally, while not shown, there is typically a coating-free area at both the inlet end 14 and the outlet end 16 of the capillary tube. The absence of the coating at the opposed ends ensures that the conductive coating does not short the high voltage power supplies that create the electrical field along the longitudinal axis of the capillary tube.

Where the first and second portions 54 and 5 of the conductive coating on a capillary tube 12 are allowed to float relative to ground, it is possible that the two portions will have different electrical potentials. This may adversely affect the reliability of an electrophoretic analysis. Alternatively, where the first and second portions 54 and 56 are to be grounded, the removal of conductive material at the detection window 52 affects continuity. As will be discussed more fully below, a third alternative to establishing an external control is to provide a potential gradient along the exterior of the capillary tube, in the same manner that a potential gradient is provided along the interior of the capillary tube. In this third alternative, the formation of the detection window 52 provides an obstacle which requires attention.

FIGS. 3 and 4 illustrate a first embodiment of a conductive bridge for providing an electrical path across the detection window 52. Here, the conductive bridge 58 is an annular member having first and second tabs 60 and 62. The capillary tube 12 is placed on the conductive bridge and aligned with the tabs. Optionally, the conductive bridge and particularly the tabs may have a trough to ensure proper alignment of the capillary tube. The conductive bridge may be a foil of aluminum or may be made of some other conductive material, such as a 0.05 inch brass flat stock. At the center of the conductive bridge is an aperture 64 to ensure that the conductive bridge does not obstruct the optical path for on-column detection of a sample through the capillary tube 12. A conductive adhesive 66 and 68 is used to secure the capillary tube to the conductive bridge. The conductive adhesive may be a nickel print.

An insulating spacer 70 is disposed above the conductive bridge 58 and the capillary tube 12. The insulating spacer is not a critical member of the present invention, but may be used to couple the on-column detector to the capillary tube while blocking external light. The insulating spacer may be made of a resilient material, such as foam rubber, so that the spacer is deformable at the area of contact with the capillary tube 12. A center aperture 72 permits passage of light along the optical path to the detection window 52. Cutaway regions 74 and 76 are aligned with the attachment of the conductive adhesive 66 and 68 to the tabs 60 and 62 of the conductive bridge 58. The electrical path across the detection window 52 that is provided by the conductive bridge 58 increases the control of electroosmotic flow through the capillary tube 12.

Figure 5:
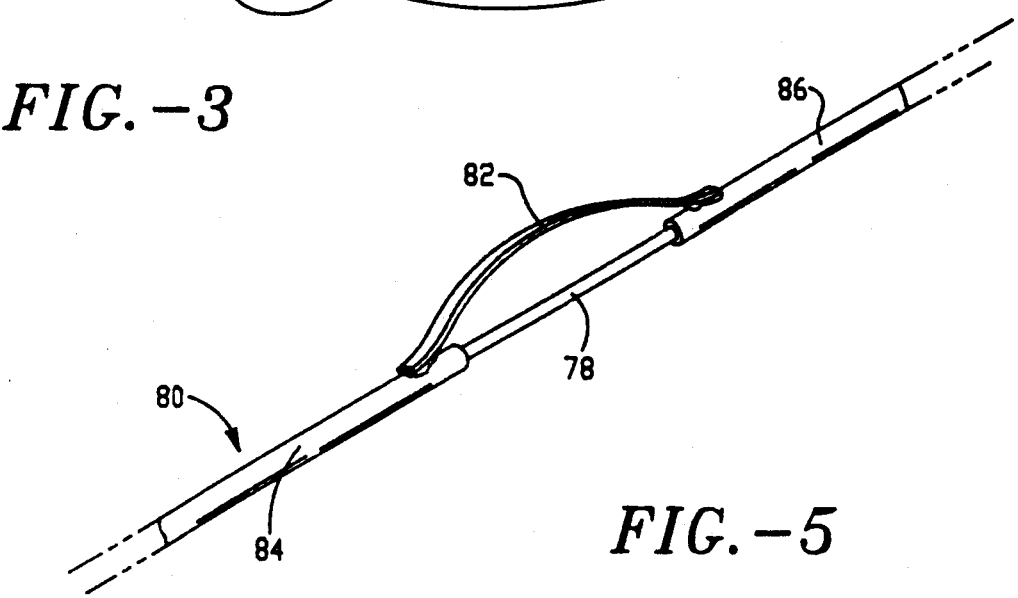
FIG. 5 is a second embodiment of a bridge for ensuring continuity of the external control structure of FIG. 1.

Referring now to FIG. 5, the second embodiment of a bridge across a detection window 78 of a capillary tube 80 is shown. The bridge is a wire 82 extending from a first portion 84 of an electrically conductive external coating to a second portion 86 of the same coating. The wire 82 may be of the type that is referred to as a "bond wire" which is conventionally used in connecting an input/output pad of an integrated circuit chip to a supporting structure such as a chip package. Alternatively, the wire 82 may be a portion of the conductive coating that is left by selective removal of the coating to form the detection window 78. Whether the wire 82 is formed of the same coating as the first and second portions 84 and 86 or is a separate member, the wire must be outside of the optical path through the detection window 78 of the capillary tube 80.

Figure 6:
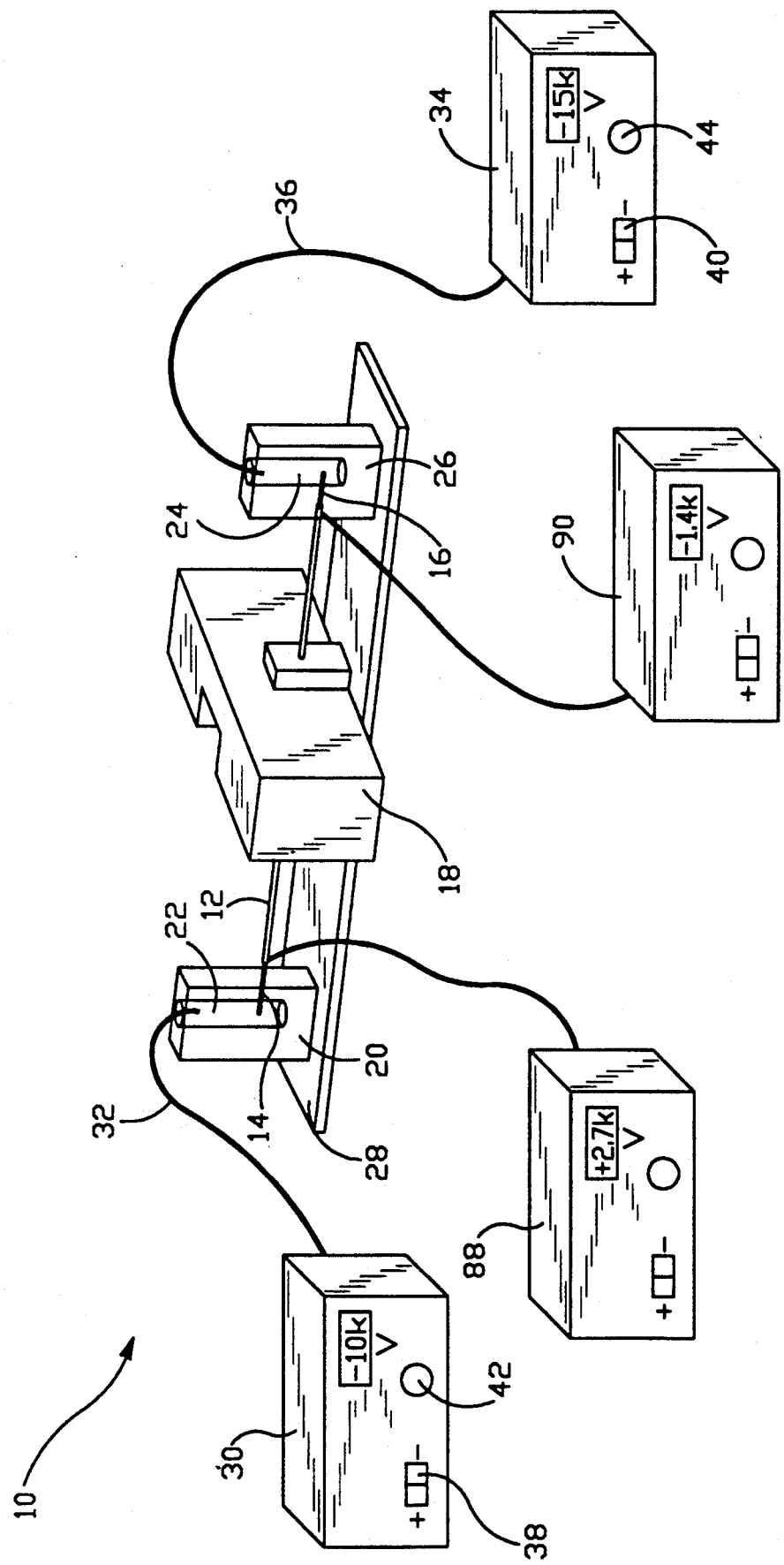
FIG. 6 is a schematic view of a second electrophoresis system having on-column detection and having external control structure for affecting the rate of electroosmotic flow.

Another embodiment of the present invention is best understood by reference to the electrophoresis system shown in FIG. 6. In addition to the first and second high voltage power supplies 30 and 34, there are third and fourth high voltage power supplies 88 and 90. The third high voltage power supply 88 is attached to the conductive coating of the capillary tube 12 at the inlet end 14 of the tube. In like manner, the fourth high voltage power supply 90 is attached at the outlet end 16. The removal of conductive coating at the inlet and outlet ends isolates the high voltage power supplies 30, 34, 88 and 90.

The potential gradient along the conductive coating of the capillary tube 12 provides a varying zeta potential at the interior of the capillary tube. This technique vectorially couples the externally applied potential with the potential across the longitudinal axis of the capillary tube 12.

The electrical potential at the exterior of the capillary tube 12 determines the polarity and the magnitude of the charged double ion layer accumulated at the interior surface of the capillary tube. That is, the potential at the tube exterior determines the zeta potential at a cross section of the tube. A practical conductive coating used successfully in the system of FIG. 6 is comprised of cross-linked polyimide containing 7.5 percent carbon black. The thickness of the coating determines the bulk resistivity and the sheet resistance. The bulk resistivity is preferably approximately 2 k ohms-cm and the sheet resistance is preferably approximately 2M ohms per square.

A concern in the system of FIG. 6 is preventing an electrical short from the conductive coating of the capillary tube 12 to the on-column detector 18. Proper insulation of the detector can guard against shorting, but another preventative measure would be to adjust the voltages of the third and fourth high voltage power supplies 88 and 90 so that the conductive coating is at ground potential at the point of detection.

Figure 7:
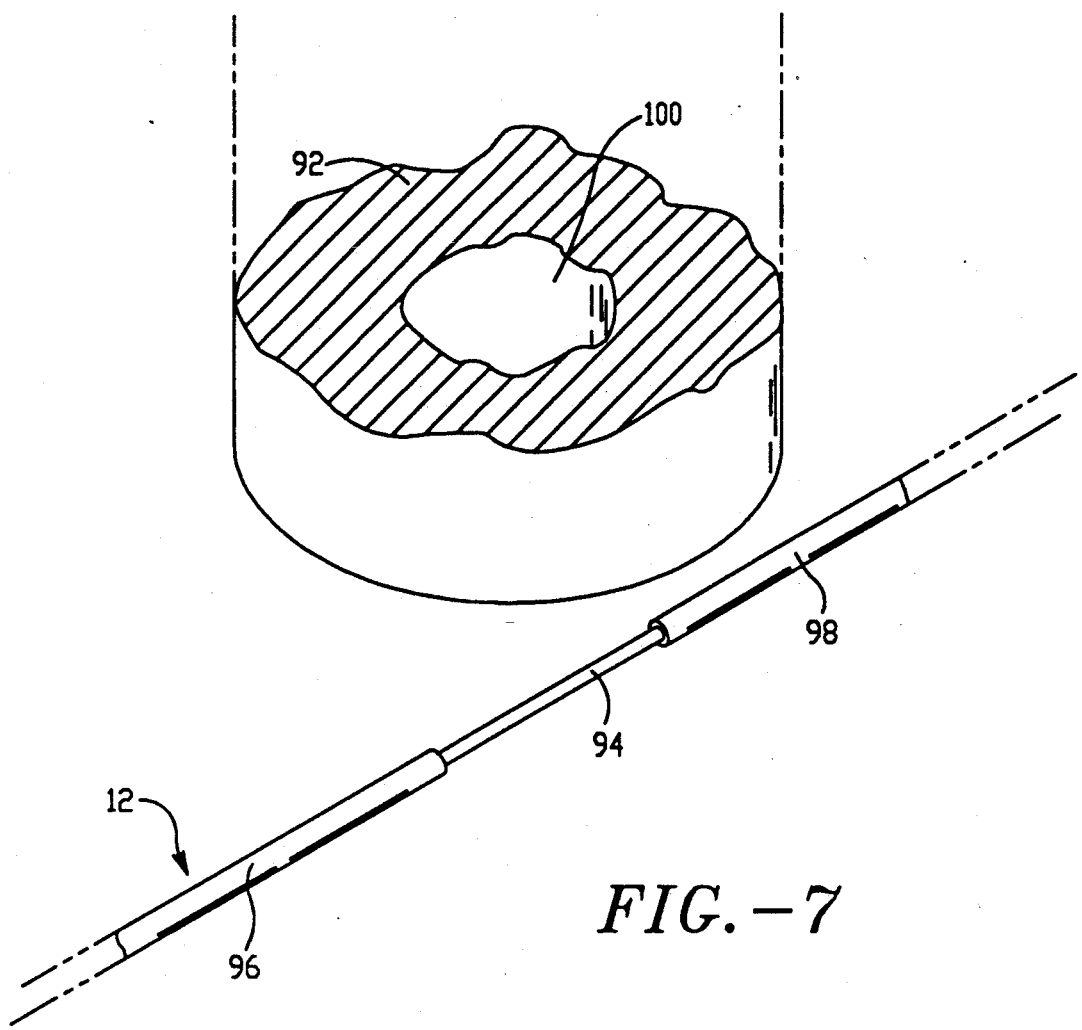
FIG. 7 is a side view of a third embodiment for ensuring continuity of external control.

Particularly where the exterior of the capillary tube 12 is at ground potential at the point of detection for the on-column detector 18, the coupling of the detector to the capillary tube can act as a bridge for electrically linking the portions of the conductive coating on opposite sides of the detection window. Referring to FIG. 7, a coupling member 92 of the on-column detector is shown. The coupling member is a metallic member having a width greater than that of the detection window 94 of the capillary tube 12. The coupling member provides the electrical path from a first portion 96 to a second portion 98 of the conductive coating on the capillary tube. An aperture 100 in the coupling member defines the optical path to the detection window 94.

While perhaps the present invention adapts most easily to use in capillary zone electrophoresis, the invention may be used with other electrophoretic separation techniques in which a capillary tube is employed. For example, the invention may be used with capillary isoelectric focusing which separates sample constituents by isoelectric point in a pH gradient formed over the length of the capillary. After the separation has been completed, electroosmotic flow may be employed in progressing the separated constituents past a detection device.

Moreover, while the capillary column has been illustrated as a single capillary tube, the separation capillary may include more than one tube and/or more than one inlet, as in the above-cited U.S. Pat. No. 4,936,974 to Rose et al.

We claim:

1. A capillary column for use in separating sample constituents by use of electroosmotic flow and electrophoretic migration comprising,
   an optically transparent tube having an inlet end and an outlet end and having a migration path for the flow of sample constituents from said inlet end to said outlet end,
   an external coating on said optically transparent tube, said external coating being opaque and being electrically conductive to allow external control of electroosmotic flow along said migration path, said external coating having an opening defining a detection window for on-column detection of sample constituents past a defined area of said migration path, said detection window providing an optical path through said external coating to said optically transparent tube at said defined area, and bridge means for providing a low resistance electrical connection across said detection window, whereby said bridge means provides a continuity of said external control of electroosmotic flow.

2. The capillary column of claim 1 wherein said external coating is in spaced apart relation from said inlet end and said outlet end of said optically transparent tube.

3. The capillary column of claim 1 wherein said bridge means includes a conductive member having a generally flat surface and an aperture aligned with said detection window.

4. The capillary column of claim 3 wherein said bridge member further includes a conductive adhesive bonding said conductive member to said external coating on opposite sides of said detector window.

5. The capillary column of claim 1 wherein said bridge means includes a wire across said detector window, said wire disposed to leave said optical path free for the passage of light.

6. The capillary column of claim 1 wherein said bridge means is a conductive member fixed to a detector, said conductive member being in electrical contact with said external coating at opposed sides of said detector window.

7. The capillary column of claim 6 wherein said conductive member is at electrical ground potential.

8. The capillary column of claim 1 wherein said external coating is slit to form first and second sides of said coating on opposite ends of said detector window, said bridge means including an optically transparent external coating at said detector window.

9. The capillary column of claim 5 wherein said wire is a portion of said external coating extending across said detector window in spaced relation to said optical path.

10. An electrophoresis system comprising, a capillary tube having a longitudinal axial bore and an outer wall, said capillary tube having an inlet end for introducing a sample solution into said longitudinal axial bore and having an outlet end, power supply means for applying a potential gradient along said longitudinal axial bore, said power supply means generating an axially-directed electrical field along said capillary tube and a radially-directed electrical field perpendicular to said longitudinal axial bore, an external control means for affecting the magnitude of said radially-directed electrical field, said external control means including an electrically conductive opaque layer on a portion of said capillary tube spaced apart from said inlet and outlet ends, said opaque layer having a slit to define an on-column detection area, said opaque layer having first and second portions on opposed sides of said slit, and an electrical path across said slit to short said first portion to said second portion, whereby said electrical path provides continuity of said external control means.

11. The system of claim 10 wherein said electrical path is a metallic member having an opening aligned with said slit to allow on-column detection.

12. The system of claim 10 wherein said electrical path is a conductive coating of transparent material linking said first portion to said second portion.

13. The system of claim 10 wherein said electrical path is a conductive wire from said first portion to said second portion.

14. The system of claim 10 further comprising a detector means having an optical path extending through said slit between said first and second portions.

15. The system of claim 14 wherein said electrical path is a conductive member attached to said detector means.

16. An improved electrophoresis system in which electroosmotic flow of a solution and differences in electrophoretic mobilities of solution constituents combine to create spatial separation of said solution constituents along a capillary tube having an inlet end and an outlet end, said electrophoresis system having a detector operatively associated with said capillary tube to detect said spatial separation at a predetermined region of said capillary tube between said inlet and outlet ends, wherein the improvement comprises, a conductive coating having first and second portions on said capillary tube, said first and second portions being spaced apart at said predetermined region and being electrically connected at said predetermined region by a lower resistance link, whereby the electrical field along said first and second portions affects electroosmotic flow along said capillary tube and said low resistance link provides a continuity of said electrical field.

17. The system of claim 16 wherein said link is a path of said conductive coating from said first portion to said second portion.

18. The system of claim 16 wherein said link is a conductive member having an opening aligned with said predetermined region for on-column detection of said spatial separation.

19. The system of claim 16 wherein said link is an electrically conductive transparent coating on said predetermined region of said capillary tube.

* * * * *